(12) United States Patent
Phillips-Hungerford et al.

(10) Patent No.: US 9,743,933 B2
(45) Date of Patent: Aug. 29, 2017

(54) RELEASE MECHANISM FOR HEMOSTASIS CLIP

(75) Inventors: Molly Phillips-Hungerford, Somerville, MA (US); Mark Wood, Shrewsbury, MA (US); Shawn Ryan, Upton, MA (US); Benjamin E. Morris, Jeffersonville, IN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1207 days.

(21) Appl. No.: 13/231,524

(22) Filed: Sep. 13, 2011

(65) Prior Publication Data

US 2012/0065646 A1 Mar. 15, 2012

Related U.S. Application Data

(60) Provisional application No. 61/382,624, filed on Sep. 14, 2010.

(51) Int. Cl.
| | |
|---|---|
| *A61B 17/10* | (2006.01) |
| *A61B 17/128* | (2006.01) |
| *A61B 17/122* | (2006.01) |
| *A61B 90/00* | (2016.01) |

(52) U.S. Cl.
CPC ........ *A61B 17/1285* (2013.01); *A61B 17/122* (2013.01); *A61B 17/128* (2013.01); *A61B 17/1227* (2013.01); *A61B 90/03* (2016.02)

(58) Field of Classification Search
CPC . A61B 17/122; A61B 17/1227; A61B 17/128; A61B 17/1285; A61B 90/03

USPC ................................ 606/139, 142, 151, 157
See application file for complete search history.

(56) References Cited

U.S. PATENT DOCUMENTS

2008/0306491 A1\* 12/2008 Cohen et al. ................. 606/142

FOREIGN PATENT DOCUMENTS

| WO | 2005/032381 | 4/2005 |
| WO | 2009/136397 | 11/2009 |
| WO | 2011/022246 | 2/2011 |

\* cited by examiner

*Primary Examiner* — Robert Lynch
(74) *Attorney, Agent, or Firm* — Fay Kaplun & Marcin, LLP

(57) ABSTRACT

Release mechanism for medical device includes a bushing having a proximal end, a distal end and a channel extending therethrough. Plurality of extend proximally from the distal end are biased toward a release configuration in which engagement surfaces at distal ends thereof retract radially into the channel. A core pin insertable through the channel applies a radially expansive pressure to move the arms radially outward to a locking configuration. Engagement surfaces of the first and second arms connect to a retaining surface of a tissue treatment device containing capsule, which extends at an angle relative to the engagement surfaces selected so that a first portion of a force transmitted along an axis of the bushing moves the arms radially inward toward the release configuration before a second portion of the force exceeds a threshold level associated with the removal of a tissue treatment device from gripped tissue.

19 Claims, 5 Drawing Sheets

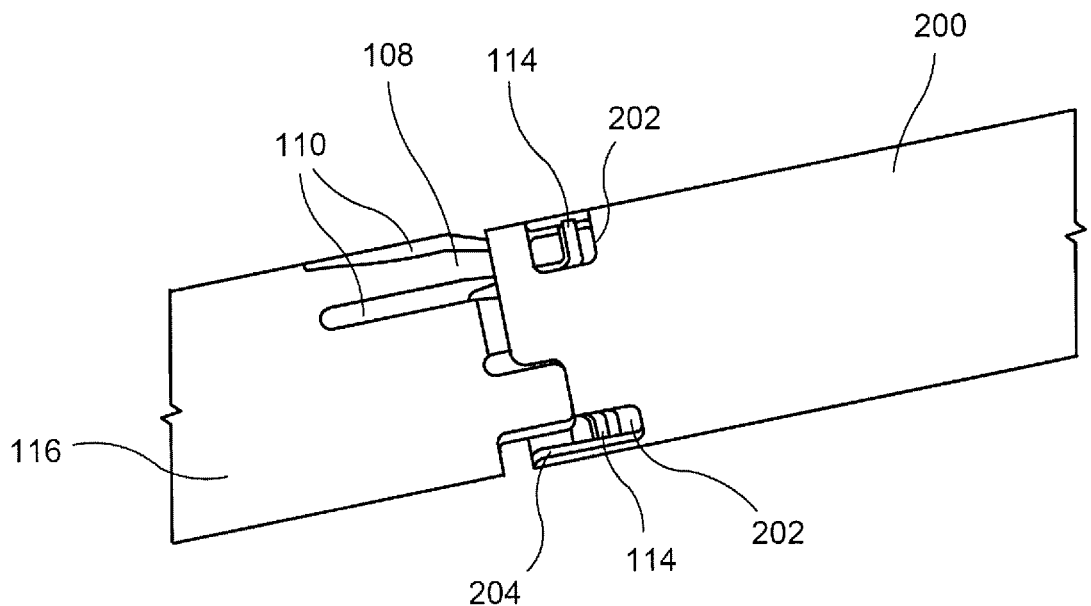
F I G. 5
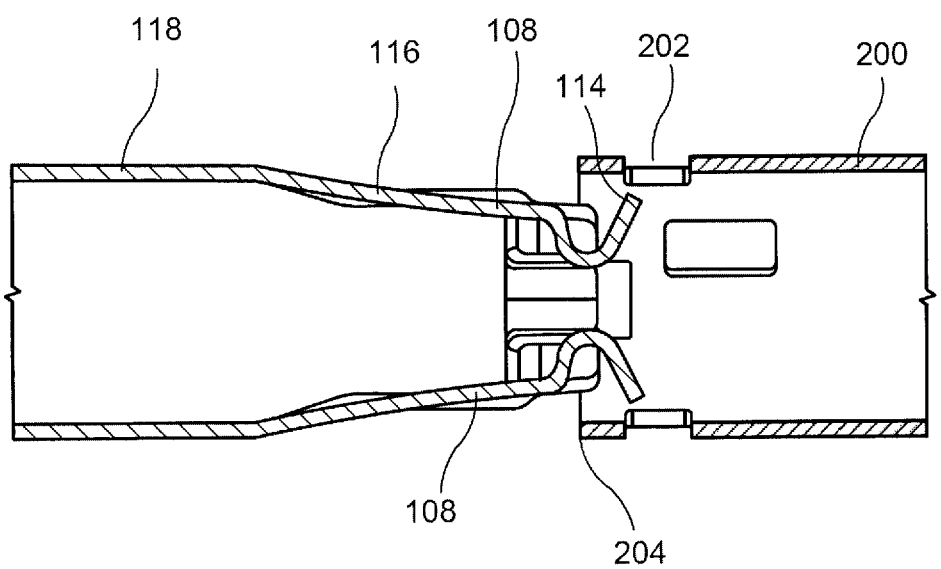
F I G. 6

RELEASE MECHANISM FOR HEMOSTASIS CLIP

PRIORITY CLAIM

The application claims the priority to the U.S. Provisional Application Ser. No. 61/382,624, entitled "Release Mechanism for Hemostasis Clip" filed Sep. 14, 2010. The specification of the above-identified application is incorporated herewith by reference.

BACKGROUND

Pathologies of the gastrointestinal ("GI") system, the biliary tree, the vascular system and other body lumens and hollow organs are often treated through endoscopic procedures, many of which require active and/or prophylactic hemostasis to control bleeding. Hemostatic clips are often deployed via endoscopes to stop internal bleeding by holding together the edges of wounds or incisions to allow natural healing processes to close the wound. Specialized endoscopic clipping devices are used to deploy the clips at desired locations of the body after which the clip delivery device is withdrawn, leaving the clip within the body. Deployment of such clips in the body is often complicated, requiring multiple steps before the clip is released from an insertion device.

SUMMARY OF THE INVENTION

The present invention is directed to a release mechanism for a medical device comprising a bushing having a proximal end, a distal end and a channel extending therethrough, the bushing comprising first and second arms extending proximally from the distal end, the first and second arms being biased toward a release configuration in which engagement surfaces at a distal ends thereof are retracted radially into the channel. The release mechanism also comprises a core pin insertable through the channel and configured to apply a radially expansive pressure to move the arms radially outward from the release configuration into a locking configuration. A clip containing capsule is connected to the bushing by engagement between the engagement surfaces of the first and second arms and a retaining surface of the capsule, the retaining surface of the capsule extending at an angle relative to the engagement surfaces selected so that a first portion of a force transmitted along an axis of the bushing to the first and second arms moves the arms radially inward toward the release configuration before a second portion of the force transmitted by the first and second arms to the capsule exceeds a threshold level associated with the removal of a clip from tissue with which it has been engaged.

BRIEF DESCRIPTION OF THE DRAWINGS

FIG. 5 shows a perspective view of the bushing of FIG. 1 in a stressed configuration;

FIG. 6 shows a partial cross-sectional view of the bushing of FIG. 1 in a non-stressed configuration.

DETAILED DESCRIPTION

Figure 1:
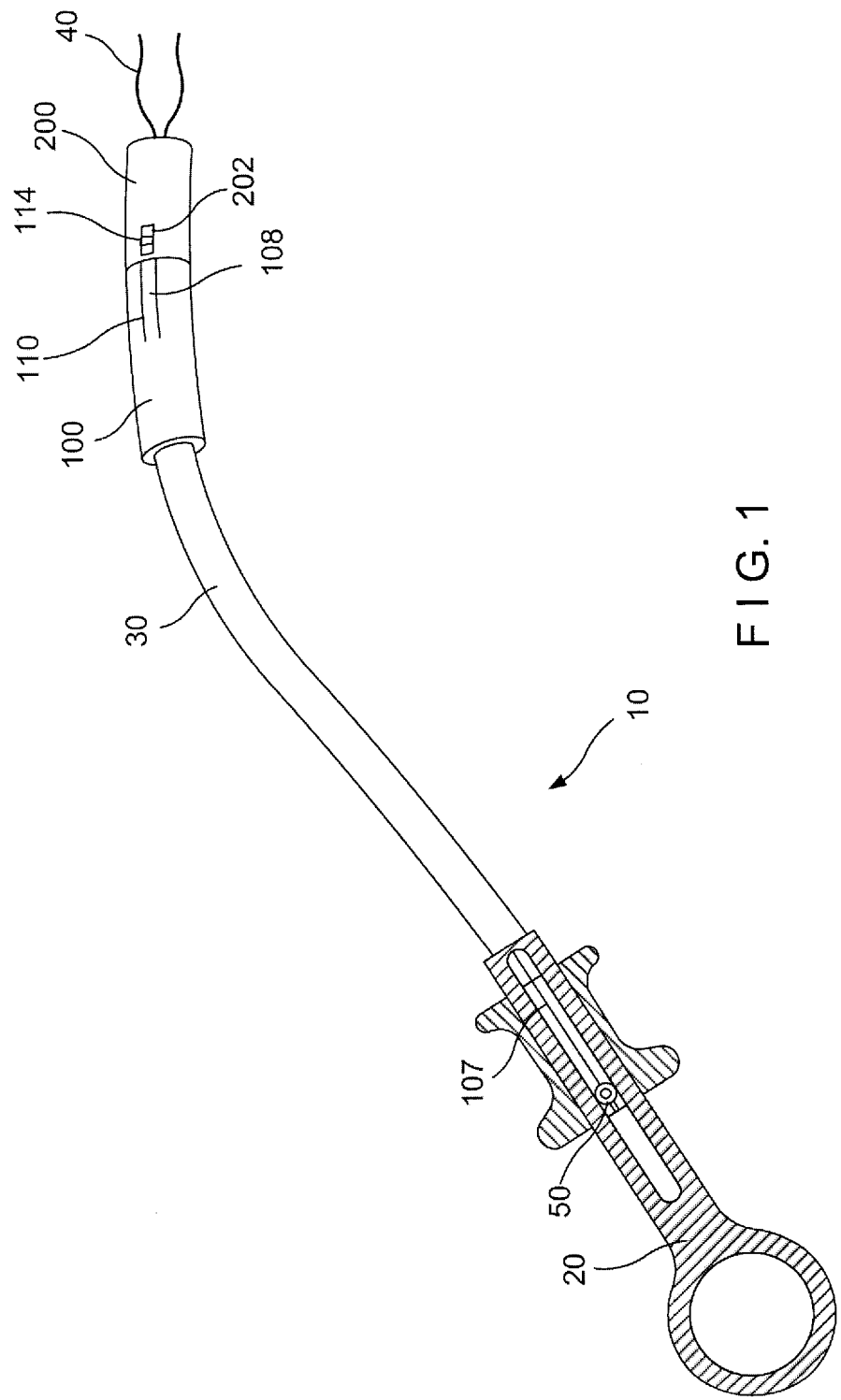
FIG. 1 shows an exemplary bushing according to the present invention in an operative configuration with a hemostatic clipping device.

The present application may be further understood with reference to the following description and the appended drawings, wherein like elements are referred to with the same reference numerals. The present invention relates to devices for hemostatic clipping and, in particular, to a hemostatic clip deployed through a single stage process. Exemplary embodiments of the present invention provide a bushing including angled bushing fingers at an end thereof to permit removable attachment of the bushing to a capsule of a hemostatic clipping device as described, for example, in U.S. Patent Application Ser. No. 60/915,806, to Adam L. Cohen, Bryan R. Ogle, Russell F. Durgin, Gregory R. Furnish, Michael Goldenbogen, Gary A. Jordan, Benjamin E. Morris, Mark A. Griffin, William C. Mers Kelly and Vasily P. Abramov filed May 7, 2007 and entitled "Single Stage Mechanical Hemostasis Clipping Device," the entire disclosure of which is hereby incorporated by reference in its entirety. The exemplary bushing of the present invention connects a capsule including a hemostatic clip to a flexible delivery member of a hemostatic clip delivery system improves a deployment mechanism usable for both single and two piece hemostatic clips as well as on a mechanism for separation of the capsule from the flexible delivery member. The exemplary embodiment of the present invention permits attachment and removal of such a clip from the bushing any number of times without breaking and without damage to the hemostatic clipping device or surrounding tissue. It is noted that embodiments of the present invention also relate to and may be employed with various types of clipping devices including, but not limited to, clips for fastening tissue layers together and clips for closing openings in one or more layers of tissue. For example, the bushing of the present invention may be used with a clipping device for closing wounds and/or incisions for hemostasis of natural or surgical bleeding, "stitching" a wound, occluding a vessel or lumen, plicating a hollow organ, attaching tissues, tissue approximation, etc. The bushing may further be used with any medical device requiring detachment from a catheter or tube.

As shown in FIGS. 1-7, a bushing 100 according to a first exemplary embodiment of the present invention comprises a substantially cylindrical body 102 extending from a proximal end 103 which is coupled to a flexible insertion member 30 of a hemostatic clipping device 10. The hemostatic clipping device 10 comprises an elongated flexible insertion member 30 extending between a proximal end coupled to a handle 20 and a distal end connected to the bushing 100. As those skilled in the art will understand, the insertion member 30 is preferably formed of a substantially flexible material to allow it to be advanced through a natural body lumen without damaging the tissue thereof and should have a length suited to the requirements of a clipping procedure being performed. The device 10 further comprises a control member 107 extending through the insertion member 30 between the handle 20 and the clip 40. The control member 107 extends from a proximal end connected to the handle 20 via a pin 50, through the bushing 100 and into the capsule 200 to a distal end connected to the clip 40. The bushing 100 of the present invention extends from a proximal end 103 coupled to a distal end of the insertion member 30 to a distal end 104 and defining a channel 106 extending therethrough. The distal end 104 comprises fingers 108 (in this example, 2 fingers 108) each of which is formed by a pair of longitudinal slits 110 extending through the cylindrical body 102. Each of the fingers 108 is biased toward a release position in which a distal ends thereof is drawn radially inward into the channel 106 out of engagement with a corresponding finger engaging window 202 in the capsule 200 an angle described in greater detail hereinafter. The fingers 108 may be formed of a material having polymer components and may be sized and shaped to exhibit predetermined deflective properties, as will be described in greater detail later. In one embodiment, the fingers 108 may be annealed or otherwise treated to exhibit the desired properties. In another embodiment, the fingers 108 may comprise holes or other portions of removed material in order to enhance their flexibility as would be understood by those skilled in the art.

Figure 2:
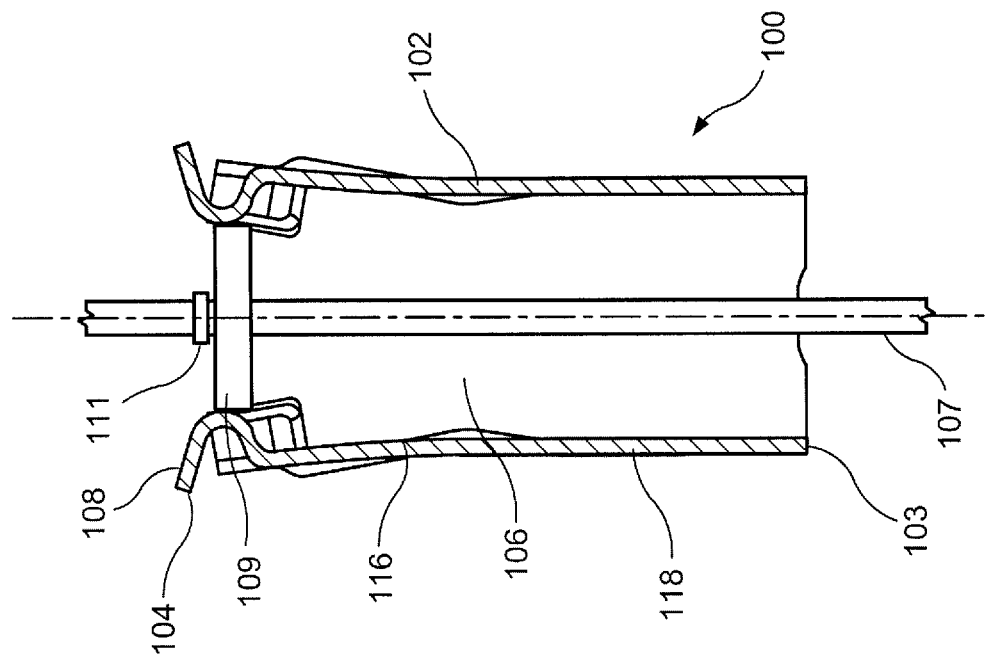
FIG. 2 shows a partial cross-sectional view of a bushing according to a first exemplary embodiment of the present invention in a biased, non-stressed configured.
Figure 3:
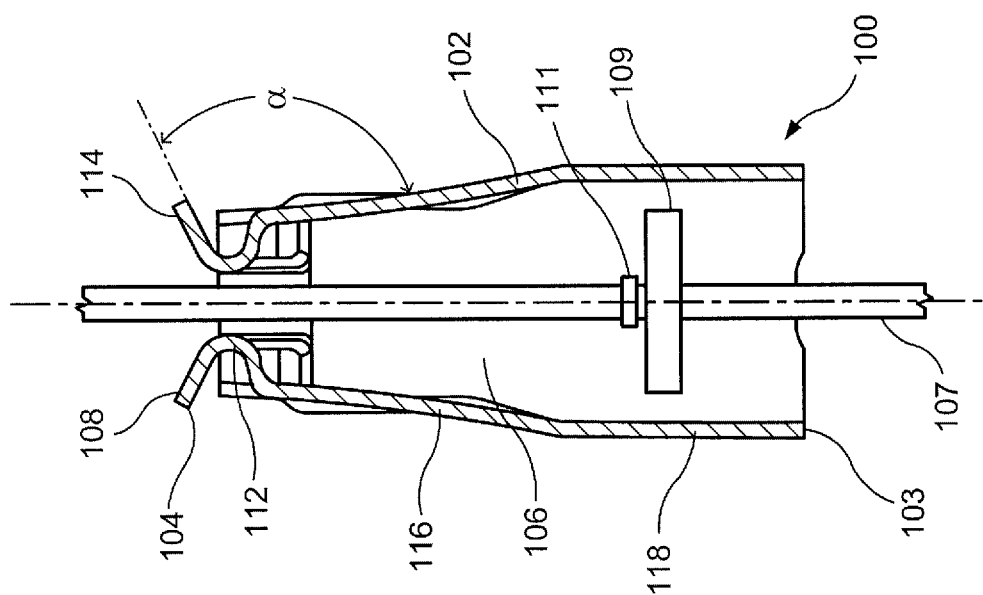
FIG. 3 shows a partial cross-sectional view of the bushing of FIG. 1 in a stressed configuration.

As shown in FIGS. 2-7, two pairs of slits 110 are formed on opposing sides of the cylindrical body 102 so that each of the fingers 108 is separated from the other by an angle of approximately 180°. As would be understood by those skilled in the art, although the bushing 100 according to this embodiment is described with two fingers, any other number of fingers may be employed without deviating from the scope of the present invention. The width of the fingers 108 is selected to permit a desired engagement between the distal end of each of the fingers 108 and the corresponding window 202. In one embodiment, the thickness of the fingers 108 is approximately 0.127 mm., although any other thickness may be used without deviating from the spirit and scope of the present invention. The material thickness of the fingers 108 is preferably selected such that a required force applied by the control member 107 to the clip 40 and subsequently, the capsule 200 does not cause the fingers 108 to disengage from the windows 202. As described above, in an unstressed state, the fingers 108 are withdrawn toward the center of the channel 106 allowing the distal end 104 of the bushing 100 to be inserted into the proximal end of a capsule 200. As will be described in greater detail with respect to the exemplary method of the present invention, a core pin 109 is inserted over the control member 107 into the bushing 100 after the distal end 104 has been inserted into the capsule 200 and advanced distally through the channel 106 to move the fingers 108 radially outward so that they engage the corresponding windows 202 of the capsule locking the busing 100 to the capsule 200. As the core pin 109 is moved into the channel 106, the fingers 108 are deflected radially outward from their unstressed state between 20 and 80 microns and more preferably by approximately 25.4-76.2 microns to lockingly engage windows 202 in the capsule 200. It is noted, however, that this range is exemplary only and that any other range may be employed without deviating from the scope of the invention. Specifically, the fingers 108 are configured so that, when in the biased configuration of FIG. 2, the bushing 100 is insertable into the capsule 200. Once inserted, the fingers 108 may be configured to deflect radially outwardly by any range. In one embodiment, the core pin 109 is formed as a disc having an outer diameter greater than a non-stressed diameter of the fingers 108, as shown in FIGS. 2 and 3, with a central opening through which the control member 107 may slide. As would be understood by those skilled in the art, the core pin 109 may be formed in any shape so long as it is sized to move through the channel 106 and is wide enough to move the fingers 108 from the unstressed position into locking engagement with the windows 202. For example, the core pin 109 may also be formed with a conical shape or any other shape without deviating from the spirit and scope of the present invention.

After the core pin 109 has been positioned to lock the bushing 100 to the capsule 200, the clip 40 may be deployed, as would be understood by those skilled in the art, by applying increasing tension to the control member 107 via the handle 20 until the connection between the clip 40 of the distal assembly and the control member 107 is severed. At this point, the core pin 109 of the control member 107 or a separate abutting member 111 attached thereto, is drawn with the control member 107 proximally through the capsule 200. The control member 107 moves proximally until the core pin 109 no longer contacts the fingers 108, thus freeing the fingers 108 to return to the unstressed position in which they are retracted radially into the channel 106 out of engagement with the windows 202 of the capsule 200. Thus, the capsule 200 is separated from the bushing 100 and the clip 40 may be left in place within the body as the bushing 100 and the control member 107 are withdrawn therefrom.

A distal end of each of the fingers 108 comprises a hook-shaped lip with a first curved section 112 extending into the channel 106 to define a reduced diameter neck of the channel 106 and a second section 114 extending distally from the first section 112. The second section 114 increases in diameter in a distal direction so that, when the core pin 109 is in position urging the fingers 108 radially outward, a diameter of the bushing 100 is greatest at a distal end of a distal section 116. In one embodiment, the bushing 100 comprises a substantially cylindrical proximal section 118 having a first substantially uniform outer diameter with a tapered distal section 116 extending therefrom tapering down in diameter in a distal direction. The second section 114 of each finger 108 extends along an axis angled relative to an axis of the distal section 116. In one embodiment, an angle $\alpha$ between the axis of the second section 114 and the axis of the distal section 116 is greater than 90° and smaller than 180° and preferably approximately 110°-115° and in an exemplary embodiment, approximately 110°.

Figure 4:
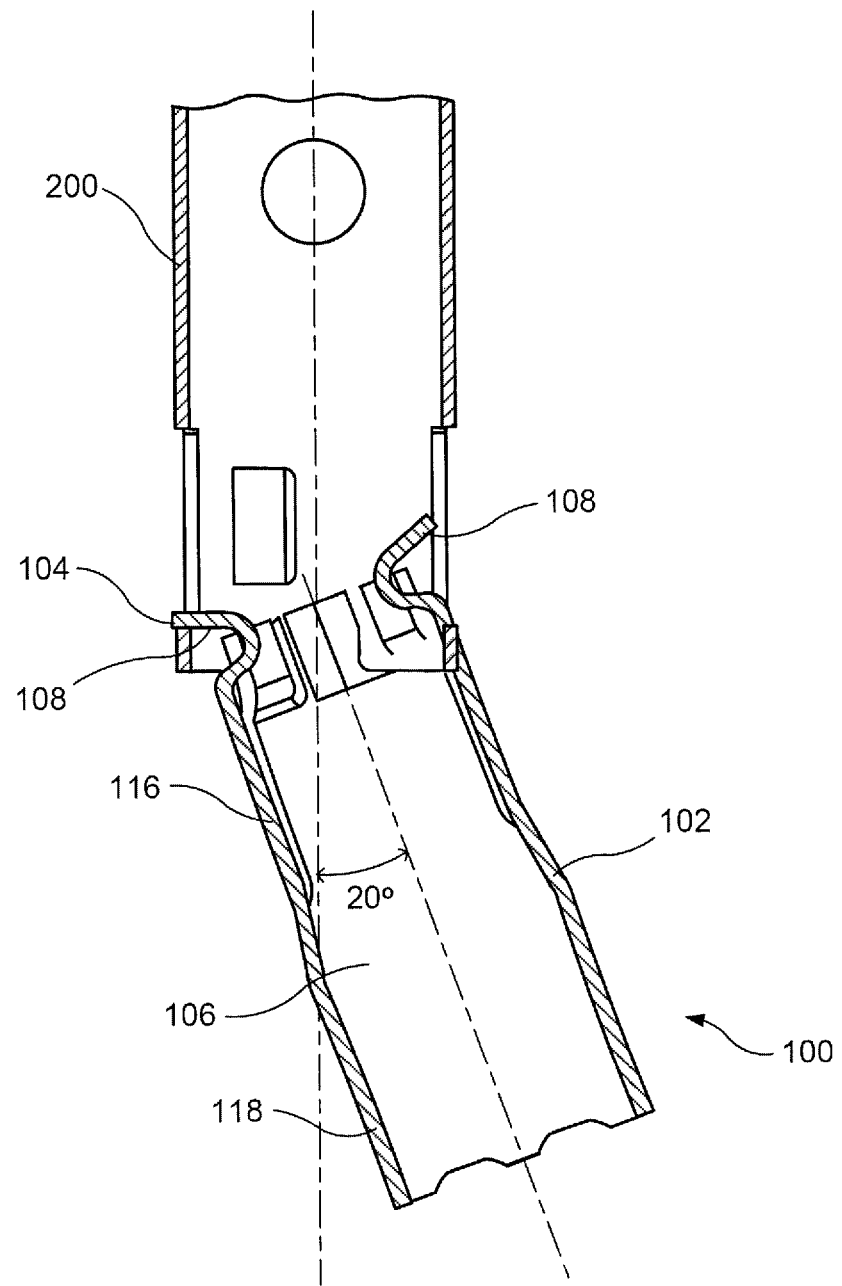
FIG. 4 shows a partial cross-sectional view of the bushing of FIG. 1 while being attached to a capsule of the hemostatic clipping device.

As described above, in an operative configuration, the first and second sections 112, 114 are configured to be received in the windows 202 formed through a proximal end 204 of the capsule 200, as shown in FIGS. 2-6. The windows 202 are formed on opposite sides of the proximal end 204 and separated from one another by an angle of approximately 180° or another angle selected to conform to the placement of the fingers 108 over the distal end 104 of the bushing 100. To couple the bushing 100 to the capsule 200, a first one of the fingers 108 is inserted into a first one of the windows 202 by pivoting the bushing 100 by, for example, approximately 20° relative to a longitudinal axis of the capsule 200 as shown in FIG. 4. It is noted however that the bushing 100 may be pivoted by any other angle as called for by the dimensions of the bushing 100, first and second sections 110, 112 and capsule 200. Once the first and second sections 110, 112 of the first finger 108 have been positioned within the first window 202, the second finger 108 is positioned adjacent to a second window 202 by returning the bushing 100 to longitudinal alignment with the capsule 200.

In operation, the bushing 100 remains coupled to the capsule 200 during insertion to a target location within a body (e.g., through a body lumen accessed via a natural body orifice). Once the capsule 200 has been properly positioned and clipped over a target portion of tissue, the user retracts the core member 107 proximally by operating the handle 20 until the control member is separated from the clip 40 (by any known mechanism) so that the control member 107 is drawn proximally to contact the core pin 109, driving the core pin 109 proximally out of engagement with the fingers 108. Proximal retraction of the core pin 107 causes the fingers 108 to return to their biased configuration in which the outer diameter of the first and second sections 110, 112 is smaller than a diameter of the capsule 200 at the windows 202.

As those skilled in the art will understand, in some cases the bushing 100 may be damaged during, for example, insertion into the body or may be otherwise deformed. In one such case, the bushing 100 may not separate from the capsule 200 upon retraction of the core pin 109 (i.e., distal ends of the fingers 108 may not be sufficiently withdrawn into the channel 106 after the core pin 109 has been removed therefrom retaining the connection between the bushing 100 and the capsule 200). The bushing according to the present invention still permits a user to separate the bushing 100 from the capsule in these situations by applying a proximally directed force to the flexible insertion member 30. That is, as the clip 40 is now locked in place on target tissue, drawing the flexible insertion member 30 proximally places the flexible insertion member 30 under tension and exerts a force on the connection between the fingers 108 of the bushing 100 and the capsule 200. The angle of the distal ends of the fingers 108 relative to the edge of the windows 202 against which they abut allows the force required to separate the bushing 100 from the capsule in these conditions to be smaller than a force required to dislodge a properly placed clip 40 from the tissue over which it has been clipped. Thus, as will be described in greater detail hereinafter, the exemplary system according to the present invention is configured so that the bushing 100 will separate from the capsule 200 when subjected to a force less than that required to pull a properly deployed clip 40 from tissue. In an exemplary embodiment of the present invention, the capsule 200 and bushing 100 may be configured with a singular connection so that, once the bushing 100 has been separated from the capsule 200, a reconnection therebetween is not permitted. In another embodiment however (not shown), the capsule 100 and bushing 200 may configured to permit multiple connections therebetween.

Figure 7:
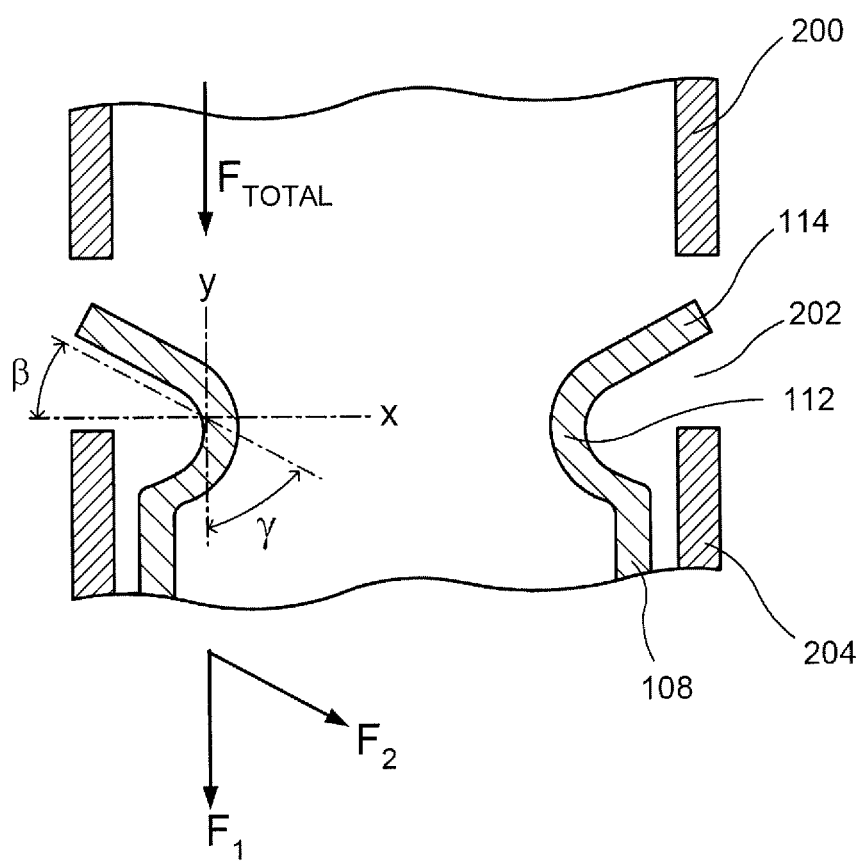
FIG. 7 shows partial cross-sectional view of the bushing of FIG. 1.

In one embodiment, as depicted in FIG. 7, the angles of the first and second sections 112, 114 convert the force $F_{TOTAL}$ to a vector force comprising a first proximally directed force, $F_1$ and a second force $F_2$ extending at an angle to the force $F_1$. As those skilled in the art will understand, the direction and magnitude of each of the forces $F_1$ and $F_2$ depend upon the configuration of the first and second sections 112, 114. In one embodiment, the second section 114 is angled with respect to the tapered distal section 116 at an angle of approximately 110-115°, as shown in FIG. 2.

The angle at which the second section 114 extends relative to the distal section 116 is selected to achieve a desired coupling strength between the capsule 200 and the bushing 100 while permitting the bushing to be pulled proximally out of engagement with the capsule 200 by a force less than that required to dislodge a clip from tissue on which it has been placed. As would be understood by those skilled in the art, the greater the angle of the second section 114 relative to the distal section 116, the smaller the force required to deflect the finger 108 radially inward out of engagement with the window 202. In an exemplary embodiment, the angle α is selected so that the force $F_2$ is sufficient to dislodge the fingers 108 from the windows 202 while the force $F_1$ remains below the level required to dislodge a deployed clip 40. In this manner, the force transmitted to the clip 40 is always less than that required to dislodge the clip 40 as the bushing 100 is disengaged from the capsule 200 before the force transmitted to the capsule exceeds this threshold level. For example, the total force required to dislodge the clip 40 from the tissue for an exemplary clip is approximately 0.947 N. However, this force may vary depending on the type of tissue being clipped, the mechanical strength of the clip 40 and a plurality of other factors known in the art. It is therefore respectfully submitted that this force is described herein for descriptive purposes only and that the angle of the second section 114 relative to the distal section 116 may be altered based on the characteristics of the procedure for which the clip 40 is intended. Each of the fingers 108 would be subject to one half of the force transmitted linearly along the insertion member 30. Where the force required to dislodge a clip 40 is 0.947 N, the force transmitted by each of the fingers 108 to the capsule 202 should be no more than 0.474 N. The desired angle of the second section 114 may then be determined using the following formulas:

$$\beta = \alpha \pm 2° - 90°,$$

wherein β is the angle of the second section 114 relative to an axis extending perpendicularly to the proximally directed force;

$$\gamma = 90° - \beta,$$

wherein γ is the complementary angle of β

$$F_2 = \cos(\gamma) \cdot 0.474 \text{ N}$$

which, when simplified, yields:

$$F_2 = \cos(180° - \alpha \pm 2°) \cdot 0.474 \text{ N}$$

From this determination, we can determine the total radial displacement each of the fingers 108 into the channel 106 upon application of the proximally directed force $F_{TOTAL}$. In one embodiment, displacement of the fingers 108 along the x-axis shown in FIG. 7 can be determined so that the distance remaining between the fingers 108 is less than the inner diameter of the capsule 200, which in an exemplary embodiment may be approximately 1.94 mm. The exact required deflection distance of the fingers 108 may vary based on an amount of damage sustained by each of the fingers 108 during manipulation. That is, if the fingers 108 return to their original configuration after engagement with the capsule 200, the amount of required deflection may be smaller than if the fingers 108 fail to recover to their neutral configuration. In one embodiment, if the angle α is selected to be 105°, β will be 15°, γ will be 75°, and $F_2$ will be 0.123 N. In this embodiment, the total displacement of each of the fingers 108 along the x-axis will be 22.86 microns. The chart below depicts a list of values for three exemplary measurements of α. It is noted that any measurement of α within the range of 90-180° is also acceptable.

| α | β | γ | $F_2$ | X-displacement |
| --- | --- | --- | --- | --- |
| 105° | 15° | 75° | 0.1227N | 22.86 μm |
| 110° | 20° | 70° | 0.1621N | 30.48 μm |
| 115° | 25° | 65° | 0.2003N | 38.1 μm |

After separating into the vector forces, the resultant force $F_1$ aids in the longitudinal separation of the fingers 108 from the windows 202 of the capsule 200, thus separating the damaged or deformed bushing 100 from the capsule 200 as depicted in FIG. 6.

It will be understood by those of skill in the art that the capsule 200 may be repeatedly moved between an engaged and disengaged position with the bushing 100 as desired by removing the core pin 109 from engagement with the fingers 108 and disengaging the fingers 108 from the windows 202 as described above. The bushing 100 may then be re-coupled to the capsule 200 when desired.

It will be apparent to those skilled in the art that various modifications can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A release mechanism for a medical device, comprising:
    a bushing having a proximal end, a distal end and a channel extending therethrough, the bushing comprising first and second arms extending proximally from the distal end, the first and second arms being biased toward a release configuration in which engagement surfaces at distal ends thereof are retracted radially into the channel;
    a core pin insertable through the channel, the core pin being configured to apply a radially expansive pressure to move the arms radially outward from the release configuration into a locking configuration; and
    a tissue treatment device containing capsule connected to the bushing by engagement between the engagement surfaces of the first and second arms and a retaining surface of the capsule, the retaining surface of the capsule extending at an angle relative to the engagement surfaces selected so that a first portion of a force transmitted along an axis of the bushing to the first and second arms moves the arms radially inward toward the release configuration before a second portion of the force transmitted by the first and second arms to the capsule exceeds a threshold level at which the tissue treatment device in the tissue treatment device containing capsule dislodges from clipped tissue, the threshold level being approximately 0.947N.

2. The release mechanism of claim 1, wherein the proximal end of the bushing is coupled to a flexible insertion member of the tissue treatment device.

3. The release mechanism of claim 2, further comprising a control member extending through the flexible insertion member from a proximal end connected to a handle of the tissue gripping device to a distal end connected to the tissue treatment device.

4. The release mechanism of claim 3, wherein a distal portion of the control member is inserted through an opening extending through the core pin, the core pin being configured so that a width of the core pin is greater than a biased width between the first and second arms.

5. The release mechanism of claim 4, wherein the core pin is disc-shaped.

6. The release mechanism of claim 4, wherein the core pin is cone shaped.

7. The release mechanism of claim 1, wherein the engagements surfaces are configured to engage the retaining surface at an angle greater than 90° and less than 180°.

8. The release mechanism of claim 7, wherein the angle is between 110° and 115°.

9. The release mechanism of claim 1, wherein the first and second arms are symmetrically disposed about an outer surface of the bushing.

10. The release mechanism of claim 9, wherein the first and second arms are separated from one another by 180°.

11. The release mechanism of claim 1, wherein the first and second arms move radially inward by between 25.4 and 76.2 microns from the locking configuration to the release configuration.

12. The release mechanism of claim 1, wherein the bushing is cylindrical.

13. The release mechanism of claim 1, wherein the engagement surfaces of the first and second arms are hook-shaped.

14. The release mechanisms of claim 1, wherein the threshold level corresponds to at least one of a type of tissue being treated and a mechanical strength of the tissue treatment device.

15. A system for releasing a tissue gripping device, comprising:
    a bushing having a proximal end, a distal end and a channel extending therethrough, the bushing comprising first and second arms extending proximally from the distal end, the first and second arms being biased toward a release configuration in which engagement surfaces at distal ends thereof are retracted radially into the channel;
    a core pin insertable through the channel, the core pin being configured to apply a radially expansive pressure to move the arms radially outward from the release configuration into a locking configuration;
    a control member extending through a flexible insertion member from a proximal end connected to a handle of the tissue gripping device to a distal end connected to the core pin;
    a tissue treatment device containing capsule connected to the bushing by engagement between the engagement surfaces of the first and second alms and a retaining surface of the capsule, the retaining surface of the capsule extending at an angle relative to the engagement surfaces selected so that a first portion of a force transmitted along an axis of the bushing to the first and second arms moves the arms radially inward toward the release configuration before a second portion of the force transmitted by the first and second arms to the capsule exceeds a threshold level at which a tissue treatment device in the tissue treatment device containing capsule dislodges from clipped tissue, the threshold level being approximately 0.947N; and
    a tissue treatment device comprising a proximal end and a tissue gripping element at a distal end.

16. The system of claim 15, wherein the engagements surfaces are configured to engage the retaining surface at an angle greater than 90° and less than 180°.

17. The system of claim 15, wherein the first and second arms move radially inward by between 25.4 and 76.2 microns from the locking configuration to the release configuration.

18. The system of claim 15, wherein the engagement surfaces of the first and second arms are hook-shaped.

19. The system of claim 15, wherein the threshold level corresponds to at least one of a type of tissue being treated and a mechanical strength of the tissue treatment device.

* * * * *